United States Patent
Sato et al.

(10) Patent No.: US 9,668,950 B2
(45) Date of Patent: Jun. 6, 2017

(54) POWDERED HAIR DYE COMPOSITION

(71) Applicant: HOYU CO., LTD., Nagoya-shi (JP)

(72) Inventors: Fumiaki Sato, Aichi-ken (JP); Emi Mori, Aichi-ken (JP); Yoshiyuki Uesawa, Aichi-ken (JP); Mikinobu Hasegawa, Aichi-ken (JP)

(73) Assignee: HOYU CO., LTD., Nagoya-Shi (JP)

( * ) Notice: Subject to any disclaimer, the term of this patent is extended or adjusted under 35 U.S.C. 154(b) by 0 days.

(21) Appl. No.: 15/027,077

(22) PCT Filed: Oct. 7, 2013

(86) PCT No.: PCT/JP2013/077268
§ 371 (c)(1),
(2) Date: Apr. 4, 2016

(87) PCT Pub. No.: WO2015/052757
PCT Pub. Date: Apr. 16, 2015

(65) Prior Publication Data
US 2016/0235634 A1    Aug. 18, 2016

(51) Int. Cl.
| | | |
|---|---|---|
| A61Q 5/10 | (2006.01) |
| A61K 8/19 | (2006.01) |
| A61K 8/73 | (2006.01) |
| A61K 8/22 | (2006.01) |
| A61K 8/02 | (2006.01) |

(52) U.S. Cl.
CPC ............... *A61K 8/19* (2013.01); *A61K 8/022* (2013.01); *A61K 8/22* (2013.01); *A61K 8/73* (2013.01); *A61K 8/731* (2013.01); *A61Q 5/10* (2013.01); *A61K 2800/4324* (2013.01)

(58) Field of Classification Search
CPC .......... A61Q 5/10; A61K 8/731; A61K 8/022; A61K 8/22; A61K 8/19; A61K 2800/4324
See application file for complete search history.

(56) References Cited

U.S. PATENT DOCUMENTS

| 4,834,768 A | 5/1989 | Grollier |
| 2002/0102225 A1 | 8/2002 | Hess et al. |
| 2002/0197223 A1* | 12/2002 | Kimura ................. A61K 8/411 424/70.1 |
| 2011/0203604 A1 | 8/2011 | Hasegawa et al. |

FOREIGN PATENT DOCUMENTS

| EP | 2361604 A | 8/2011 |
| JP | 6019712 A | 1/1985 |
| JP | 08239313 A | 9/1996 |
| JP | 0967235 A | 3/1997 |
| JP | 11246370 A | 9/1999 |
| JP | 2001253812 A | 9/2001 |
| JP | 2002097120 A | 4/2002 |
| JP | 2003104856 A | 4/2003 |
| JP | 2003238369 A | 8/2003 |
| JP | 2004091431 A | 3/2004 |
| JP | 2010260837 A | 11/2010 |

OTHER PUBLICATIONS

International Search Report, PCT/JP2013/077268, Jan. 7, 2014, pp. 1-2.
European Search Report dated Mar. 28, 2017, 6 pages, received during prosecution of the corresponding European patent application No. 13895185.0.

* cited by examiner

*Primary Examiner* — Eisa Elhilo
(74) *Attorney, Agent, or Firm* — Cantor Colburn LLP

(57) ABSTRACT

A powder hair dye composition includes component (A) to component (C). The content of the component (A) at the time of use is 1 to 5 mass %. The component (A) is sodium percarbonate. The component (B) is sodium carboxymethyl cellulose. The component (C) is a thickener other than the component (B).

3 Claims, No Drawings

POWDERED HAIR DYE COMPOSITION

BACKGROUND OF THE INVENTION

The invention disclosed in this application relates to a powder hair dye composition. The invention specifically relates to a powder hair dye composition containing sodium percarbonate, which is an oxidizing agent, as an essential component, and also containing sodium carboxymethyl cellulose, which is a thickener, as an essential component.

"Hair dye composition" at least encompasses "oxidation hair dye" and "hair bleach".

"Oxidation hair dye" is used for the purpose of dyeing hair, and it at least contains an oxidizing agent and an oxidation dye and usually also contains an alkaline agent. An oxidation dye is composed of a key intermediate or of a key intermediate and a coupler. When an oxidation hair dye is allowed to act on the hair, melanin in the hair is decomposed by the action of the oxidizing agent, and also the oxidation dye is polymerized in the hair to form an oxidized dye polymer, whereby the hair is dyed to the desired hue. In an oxidation hair dye, a direct dye is sometimes incorporated for adjusting the hue of the dyed hair.

"Hair bleach" is used for the purpose of bleaching hair, and it at least contains an oxidizing agent and usually also contains an alkaline agent. When a hair bleach is allowed to act on the hair, melanin in the hair is decomposed by the action of the oxidizing agent, and the hair is bleached to a lighter color.

"Powder hair dye composition" is a powdered formulation of a hair dye composition, and the above oxidizing agent, oxidation dye, alkaline agent, and like components are also incorporated in powder form. Powder hair dye compositions are usually one-agent type, but may also be multi-agent type such as two- or more-agent type. At the time of use, a powder hair dye composition is mixed with a liquid medium such as water to form a hair dye solution for application and then applied to the hair.

Composition used for hair dyeing is categorized into temporary hair colors, semi-permanent hair colors, and permanent hair colors.

An oxidation hair dye is one of permanent hair colors. Oxidation hair dyes have excellent hair-dyeability and fastness (color sustainability) and thus are currently most commonly used. Incidentally, a hair bleach also contains an oxidizing agent, and thus hair bleaches are structurally close to permanent hair colors.

The oxidation hair dye is usually composed of a first agent in cream or liquid form containing an oxidation dye and a second agent in cream or liquid form containing an oxidizing agent. At the time of use, the first agent and the second agent are mixed and then applied to the hair to dye the hair.

Meanwhile, as another form of oxidation hair dye, those in powder form are known. Such a hair dye incorporates an oxidation dye and an oxidizing agent in the form of powders, and is mixed with a liquid medium such as water and then applied to the hair to dye the hair.

Therefore, in this application, "at the time of use" regarding a powder hair dye composition means the state in which the powder hair dye composition has been mixed with a liquid medium such as water. Meanwhile, "at the time of storage" means the state in which the composition is in powder form.

Powder hair dye compositions are characterized in that, as described above, they are easy to use, are lightweight and thus convenient to transport or carry, and can be used in portions, for example.

The following PTL 1 discloses a powder hair dye composition incorporating a sulfate or hydrochloride of N,N-bis(β-hydroxyethyl)-p-phenylene diamine, which is an oxidation dye, and an oxidizing agent. It is stated that as the oxidizing agent, percarbonates and perborates are equally preferable (PTL 1, paragraph 0009).

The following PTL 2 discloses a powder hair dye composition incorporating a dye, an oxidizing agent, and a dispersant. It is stated that as the oxidizing agent, percarbonates and perborates are equally preferable (PTL 2, paragraph 0008).

CITATION LIST

Patent Literature

PTL 1: JP-A-8-239313
PTL 2: JP-A-11-246370

SUMMARY OF INVENTION

In some of the examples described in the above PTL 1 and PTL 2, sodium carboxymethyl cellulose is incorporated as a thickener.

However, there has been a problem in that when sodium carboxymethyl cellulose is incorporated in a powder hair dye composition incorporating sodium percarbonate, the viscosity at the time of use decreases during long-term storage. A decrease in viscosity is problematic in that the hair dye composition at the time of use (hair dye solution for application in the below Examples) is likely to fall down from the hair or the application tool such as a brush. It has been believed that carboxymethyl cellulose is affected by sodium percarbonate during storage, and thus viscosity suitable for use cannot be obtained after long-term storage.

However, this problem has occurred in the case of using sodium percarbonate as an oxidizing agent. The above PTL 1 and PTL 2 state that percarbonates and perborates have equal properties as preferred oxidizing agents. However, the above problem does not occur even when a perborate and sodium carboxymethyl cellulose are used together.

Meanwhile, in a powder hair dye composition incorporating sodium percarbonate, in the case where xanthan gum is used as a thickener, the viscosity at the time of use is unlikely to decrease during long-term storage as above. However, the use of xanthan gum alone as a thickener has been problematic in that, in the first place, the miscibility with a liquid medium such as water is insufficient, and also the operability including the adhesion to the hair, a brush, or the like, the spread upon application, etc., is insufficient.

The present inventors have conducted extensive research in order to solve the above problems. As a result, they have accomplished the invention disclosed in this application, in which sodium percarbonate, sodium carboxymethyl cellulose, and another thickener is used together, and the content of sodium percarbonate at the time of use is within a certain range.

An object to be achieved is to provide a powder hair dye composition having excellent miscibility with a liquid medium such as water, excellent operability at the time of application to hair, and excellent temporal stability during long-term storage.

Another object to be achieved is to provide a method for dyeing hair using the powder hair dye composition, which offers excellent operability at the time of application to hair. According to the method for dyeing hair, as long as certain conditions, such as to use the powder hair dye composition disclosed in this application, are satisfied, the operability is excellent even when the powder hair dye composition is used after long-term storage.

(First Invention)

A first invention of this application for solving the above problems is a powder hair dye composition including the following component (A) to component (C), the content of the component (A) at the time of use being 1 to 5 mass %:

(A) sodium percarbonate;
(B) sodium carboxymethyl cellulose;
(C) a thickener other than the component (B).

In this application, "content at the time of use" means a content in the state in which the composition has been mixed with a liquid media such as water.

(Second Invention)

A second invention of this application for solving the above problems is the powder hair dye composition according to the first invention, wherein the powder hair dye composition satisfies the following conditions (1) and/or (2):

(1) the content of the component (B) at the time of use is 0.8 to 3 mass %;
(2) the content of the component (C) at the time of use is 0.4 to 1.5 mass %.

The second invention may satisfy only the condition (1) or may alternatively satisfy only the condition (2). In addition, it may also satisfy both of the conditions (1) and (2).

(Third Invention)

A third invention of this application for solving the above problems is the powder hair dye composition according to the first invention or the second invention, wherein the total content of the component (B) and the component (C) is 1.5 to 3 mass % at the time of use.

(Fourth Invention)

A fourth invention of this application for solving the above problems is a method for dyeing hair using a powder hair dye composition containing the component (A) to component (C), wherein hair dyeing is performed with the content of the component (A) at the time of use being 1 to 5 mass %.

(Fifth Invention)

A fifth invention of this application for solving the above problems is the method for dyeing hair according to the fourth invention, wherein the method satisfies the following conditions (3) and/or (4):

(3) the content of the component (B) at the time of use is 0.8 to 3 mass %;
(4) the content of the component (C) at the time of use is 0.4 to 1.5 mass %.

(Sixth Invention)

A sixth invention of this application for solving the above problems is the method for dyeing hair according to the fourth invention or the fifth invention, wherein the total content of the component (B) and the component (C) is 1.5 to 3 mass % at the time of use.

Advantageous Effects of Invention

The powder hair dye composition disclosed in this application has excellent miscibility with a liquid medium such as water, excellent operability at the time of application to hair, and excellent temporal stability during long-term storage.

The method for dyeing hair disclosed in this application is a method for dyeing hair, which offers excellent operability at the time of application to hair. According to the method for dyeing hair, as long as certain conditions, such as to use the powder hair dye composition disclosed in this application, are satisfied, the operability is excellent even when the powder hair dye composition is used after long-term storage.

DETAILED DESCRIPTION OF THE PREFERRED EMBODIMENTS

Hereinafter, embodiments of the invention disclosed in this application will be described, including the best mode.

[Powder Hair Dye Composition]

This application discloses a powder hair dye composition including the following component (A) to component (C), the content of the component (A) at the time of use being 1 to 5 mass %:

(A) sodium percarbonate;
(B) sodium carboxymethyl cellulose;
(C) a thickener other than the component (B).

[Component (A)]

The component (A) is sodium percarbonate. In the powder hair dye composition disclosed in this application, the content of the component (A) at the time of use is 1 to 5 mass %. Such a content makes it easy to dye the hair into a deep hue, such as deep black. When the content of the component (A) is more than 5 mass %, the amount of component (A) at the time of storage becomes excessive, resulting in insufficient temporal stability during long-term storage.

Incidentally, as the object to which the powder hair dye composition disclosed in this application is applied, human hair, particularly the head hair, is preferable. The object is more preferably white hair, gray hair, or black hair.

In terms of making the amount of component (A) at the time of storage within the suitable range and improving the temporal stability, the upper limit of the content of the component (A) at the time of use may be 4 mass % or may be 3 mass %. Like this, when the content of a component at the time of use is suitable, it becomes easy to make the content of the component at the time of storage within a preferred range.

In powder state (at the time of storage), in terms of improving the temporal stability during long-term storage, the content of the component (A) may be 11 to 55 mass % or may be 11 to 44 mass %.

[Component (B)]

The component (B) is sodium carboxymethyl cellulose. A powder hair dye composition containing the component (B) is advantageous in that such a composition is unlikely to aggregate even when mixed with a liquid medium such as water. In other words, the powder hair dye composition containing the component (B) has excellent dispersibility/solubility in a liquid medium such as water.

In addition, the powder hair dye composition containing the component (B) spreads well when applied and also has excellent adhesion to the hair, a brush, or the like.

In the powder hair dye composition disclosed in this application, the content of the component (B) at the time of use is not particularly limited. In terms of well ensuring the advantageous effects of the invention disclosed in this application, the content of the component (B) at the time of use is preferably 0.8 to 3 mass %, and more preferably 1.4 to 3 mass %.

[Component (C)]

The component (C) is a thickener other than the component (B). There is a problem in that when the above sodium percarbonate and the above sodium carboxymethyl cellulose are merely used together, the viscosity at the time of use decreases during long-term storage. Thus, a thickener other than the component (B) is further used together, thereby improving the temporal stability during long-term storage.

Thickeners corresponding to as the compound (C) can be suitably selected provided that the advantageous effects of the invention disclosed in this application are exerted. Specific examples of the component (C) include seaweed, sodium alginate, methyl cellulose, hydroxyethyl cellulose, polyvinyl alcohol, polyvinyl pyrrolidone, sodium polyacrylate, guar gum, xanthan gum, tragacanth gum, quaternary-nitrogen-containing cellulose ethers such as hydroxyethyl cellulose dimethyldiallylammonium chloride and hydroxyethyl cellulose hydroxypropyltrimethylammonium chloride, cationized polymers such as polyquaternium-10 and guar hydroxypropyltrimonium chloride, anionic associative polymers such as highly polymerized polyethylene glycols and carboxyvinyl polymers, and anionic non-associative polymers such as acrylate-alkyl methacrylate copolymers. The component (C) may be one or more kinds of them.

It is preferable that the component (C) is one or more kinds selected from xanthan gum, hydroxyethyl cellulose, cationized polymers, highly polymerized polyethylene glycols (preferably polyethylene glycol having a number average molecular weight of 100,000 to 7000,000), anionic associative polymers, and anionic non-associative polymers. In terms of improving the miscibility with a liquid medium such as water, the operability at the time of application to hair, and the temporal stability during long-term storage in a well-balanced manner, the component (C) is more preferably one or more kinds selected from xanthan gum, hydroxyethyl cellulose, and cationized polymers, still more preferably xanthan gum. Xanthan gum is preferable also in terms of suppressing the deterioration of operability during long-term storage.

In the powder hair dye composition disclosed in this application, the content of the component (C) at the time of use is not particularly limited. In terms of well ensuring the advantageous effects of the invention disclosed in this application, the content of the component (C) at the time of use is preferably 0.4 to 1.5 mass %, and more preferably 0.4 to 1.2 mass %.

[Component (B) and Component (C) at Time of Use]

In the powder hair dye composition disclosed in this application, the total content of the component (B) and the component (C) at the time of use is not particularly limited. In terms of improving the miscibility with a liquid medium such as water, the operability at the time of application to hair, and the temporal stability during long-term storage in a well-balanced manner, it is preferable that the total content of the component (B) and the component (C) at the time of use is 1.5 to 3 mass %. In powder state (at the time of storage), the total content of the component (B) and the component (C) may be 18 to 40 mass % or may be 18 to 30 mass %.

In the powder hair dye composition disclosed in this application, the content ratio on mass basis between the component (B) and the component (C) at the time of use is not particularly limited. The content ratio on mass basis may be as follows: component (B):component (C)=5:1 to 1:2.

In addition, also in powder state (at the time of storage), the content ratio on mass basis may be as follows: component (B):component (C)=5:1 to 1:2.

[Oxidizing Agent Other than Component (A)]

In addition to the component (A), the powder hair dye composition disclosed in this application may contain other optional oxidizing agents. Examples of optional oxidizing agents include potassium percarbonate, various perborates, various peroxide salts, hydrogen peroxide adducts of various sulfates, hydrogen peroxide adducts of various phosphates, hydrogen peroxide adducts of various pyrophosphates, urea peroxide, melamine peroxide, various perbromates, and various permanganates.

In the case where the component (A) and optional oxidizing agents are used together, in terms of providing the treated hair with a deep hue, it is preferable that the total content of oxidizing agents at the time of use is 5 mass % or less.

In addition, in terms of improving the temporal stability during long-term storage, in powder state (at the time of storage), it is preferable that the total content of oxidizing agents is 55 mass % or less.

Incidentally, it is also preferable that the component (A) is used as only oxidizing agent.

[Alkaline Agent]

A powder hair dye composition usually contains an alkaline agent. The powder hair dye composition disclosed in this application contains sodium percarbonate as an essential component. When mixed with a liquid media such as water, powder sodium percarbonate is decomposed to produce sodium carbonate, which is an alkaline agent.

The powder hair dye composition disclosed in this application may further contain optional powder alkaline agents. Examples of optional alkaline agents include sodium carbonate, magnesium carbonate, sodium metasilicate, basic amino acid, ammonium hydrogencarbonate, sodium hydrogencarbonate, potassium hydrogencarbonate, ammonium carbamate, potassium carbonate, guanidine carbonate, lithium carbonate, calcium carbonate, and ammonium sulfate.

Incidentally, it is also preferable that the powder hair dye composition disclosed in this application does not contain optional powder alkaline agents.

[Dye]

The powder hair dye composition disclosed in this application may contain an oxidation dye. The oxidation dye is composed of a key intermediate or of a key intermediate and a coupler. The powder hair dye composition disclosed in this application may contain one or more kinds selected from key intermediates and couplers that can be prepared in powder form. The above sodium percarbonate has relatively high reactivity, and thus, in terms of well dyeing the hair even after long-term storage, it is preferable that the oxidation dye is a sulfate.

Examples of key intermediates include paraphenylenediamine sulfate, toluene-2,5-diamine sulfate, paraaminophenol sulfate, orthoaminophenol sulfate, 2,2'-[4(-aminophenyl)imino]bisethanol sulfate, 1-hydroxyethyl-4,5-diaminopyrazole sulfate, and hydroxyethyl paraphenylenediamine sulfate.

Examples of couplers include 5-aminoorthocresol sulfate, methaminophenol sulfate, 2,6-diaminopyridine sulfate, 2,4-diaminophenoxyethanol sulfate, paramethylaminophenol sulfate, 5-(2-hydroxyethylamino)-2-methylphenol sulfate, and metaphenylenediamine sulfate.

In addition to the above oxidation dyes, known direct dyes, such as nitro dyes, azo dyes, nitroso dyes, triphenylmethane dyes, xanthene dyes, quinoline dyes, anthraquinone dyes, and indigo dyes, may be also incorporated in the powder hair dye composition.

Meanwhile, the powder hair dye composition disclosed in this application may also be formed as a hair bleach without containing an oxidation dye and a direct dye.

[Other Components]

In addition to the above components, the powder hair dye composition disclosed in this application may suitably contain other optional components. For example, dispersants, oil components, sodium sulfate, surfactants, polypeptides, pH adjusters, and the like may be suitably selected and incorporated in suitable amounts.

Examples of dispersants include metal stearates such as magnesium stearate, silicic acid, metal silicates, talc, sucrose fatty acid esters, and lactose, and metal stearates are particularly preferable.

As oil components, those in liquid form having fluidity at normal temperature are preferably used. Examples of oil components include α-olefin oligomer, light isoparaffin, light liquid isoparaffin, squalane, synthetic squalane, vegetable squalane, liquid isoparaffin, liquid paraffin, and silicone oil.

Sodium sulfate is incorporated in order to prevent performance degradation due to the moisture absorption of the powder hair dye composition. The amount thereof to be incorporated may be suitably determined.

Examples of surfactants include higher alkylbenzene sulfonates, fatty acid soaps, higher alkyl sulfonates, higher alkyl phosphates, and higher alkyl sulfosuccinates.

Examples of polypeptides include hydrolysates prepared by treating collagen, keratin, elastin, fibroin, conchiolin, soybean protein, casein, or a like protein with an acid, an alkali, an enzyme, or the like, as well as quaternized cation-modified proteins.

Examples of pH adjusters include ammonium nitrate, ammonium carbonate, ammonium chloride, primary ammonium phosphate, secondary ammonium phosphate, citric acid, tartaric acid, lactic acid, and succinic acid.

Further, as optional components in solid form, antistatic agents, hair softeners, antioxidants, preservatives, vehicles, pigments, perfumes, sequestering agents, humectants, moisturizers, and the like may be suitably incorporated.

[Production Method, Etc.]

The powder hair dye composition disclosed in this application can be prepared in the usual manner. In the case of a powder hair dye composition containing an oil component in liquid form having fluidity at normal temperature, for example, it is possible that raw material powders other than the oil component are each dried and then mixed, and the oil component is sprayed thereto, thereby producing the powder hair dye composition.

The powder hair dye composition disclosed in this application may be placed and stored in a storage container conventionally used for powder hair dye compositions. It is preferable that the storage container includes at least one layer selected from a polyethylene layer, a polypropylene layer, an acrylonitrile-styrene layer, a polyethylene terephthalate layer, a polystyrene layer, a polyvinyl chloride layer, a polycarbonate layer, a polyvinyl alcohol layer, a nylon layer, a cellophane layer, and a polyvinylidene chloride layer. The storage container may have a monolayer structure or may also have a multilayer structure including two or more layers. It is preferable that the container wall thickness of the storage container is within a range of 0.5 to 2 mm.

[Use of Powder Hair Dye Composition]

At the time of use, the powder hair dye composition disclosed in this application is mixed with a liquid medium such as water and then applied to the hair. The liquid medium is preferably water such as tap water, purified water, deionized water, or distilled water, or a water-based liquid medium. It is more preferably water.

The mixing ratio on mass basis between the powder hair dye composition and the liquid medium is preferably as follows: powder hair dye composition:liquid medium=1:7 to 1:15, more preferably 1:8 to 1:12. Such a mixing ratio makes it easy to dye the hair to a deep hue, such as deep black, while suitably suppressing the bleaching power of the powder hair dye composition. Also in terms of well ensuring the advantageous effects of the invention disclosed in this application, it is preferable that the powder hair dye composition is used in the preferred mixing ratio.

The pH at the time of use is not particularly limited. In terms of making it easier to dye the hair to a deep hue, such as deep black, the pH at the time of use is preferably 10 or less, and more preferably 6 to 10.

It is preferable that the viscosity at the time of use is 1,000 to 30,000 mPa·s. Incidentally, the viscosity at the time of use can be measured using a B-type viscometer with reference to the below Examples.

The powder hair dye composition disclosed in this application can be suitably used in the usual manner. For example, the powder hair dye composition is mixed with a liquid medium such as water to form a hair dye solution for application in paste form, and then applied to the hair using a comb, a brush, or the like.

The leave-on time after the application to the hair is not particularly limited, and may be about 30 to 40 minutes. After being left on like this, the hair dye solution for application adhering to the hair is rinsed off. Subsequently, the hair may be suitably treated with a shampoo, a conditioner, or the like.

[Method for Dyeing Hair]

As described above, this application also discloses a method for dyeing hair using a powder hair dye composition containing the component (A) to component (C), wherein hair dyeing is performed with the content of the component (A) at the time of use being 1 to 5 mass %.

In the method for dyeing hair, the above disclosure of the powder hair dye composition can be taken into consideration.

EXAMPLES

Hereinafter, examples will be described. The technical scope of the invention disclosed in this application is not limited to the following examples.

First, tables will be explained. For components corresponding to the components (A) to (C) of this application, the corresponding alphabets A to C are given beside the respective component names.

The unit of values to represent the content of each component shown in the tables is mass %.

The "Content of component A at the time of use" column shows the content of the component (A) in a hair dye solution for application.

The "Total content of component B and component C at the time of use" column shows the total content of the component (B) and the component (C) in a hair dye solution for application.

The "B/C" column shows the content ratio on mass basis between the component (B) and the component (C) in a powder hair dye composition. The content ratio is maintained also in the resulting hair dye solution for application.

The unit of values shown in the "Viscosity" column is mPa·s. The viscosity is the viscosity of a hair dye solution for application prepared in the following mixing ratio on mass basis using a powder hair dye composition immediately after preparation: "powder hair dye composition:water=1:10".

The viscosity was measured using a B-type viscometer (VISCOMETER TV-10 (manufactured by Toki Sangyo Co., Ltd.)) under the following conditions: 25° C., 1 minute, rotational speed: 12 rpm, No. 4 rotor used.

[Preparation of Powder Hair Dye Composition]

The one-agent type powder hair dye compositions of Examples 1 to 13 shown in the below Table 1 and Table 2 and those of Comparative Examples 1 to 3 shown in the below Table 3 were prepared in the usual manner. Example 13 is a hair bleach, while other examples and comparative examples are oxidation hair dyes.

[Miscibility Test]

To 3 g of the powder hair dye composition of each of Examples 1 to 13 and Comparative Examples 1 to 3 immediately after preparation, 30 ml of water was added and mixed. The mixing ratio is, on mass basis, as follows: powder hair dye composition:water=1:10. Miscibility at this time was evaluated based on the following criteria.

5: They can be mixed well uniformly.
  4: They can be mixed almost uniformly.
  3: They can be mixed.
  2: They are slightly hard to mix.
  1: They are hard to mix and non-uniform.

For each test, ten panelists performed the evaluation, and the average was rounded to the nearest whole number and shown in the table as a whole number.

[Operability Test]

To 3 g of the powder hair dye composition of each of Examples 1 to 13 and Comparative Examples 1 to 3 immediately after preparation, 30 ml of water was added and mixed to give a hair dye solution for application. In the operation of applying each hair dye solution for application to human head hair using a brush, the operability was evaluated based on the following criteria.

5: The solution for application is extremely easy to scoop with a brush, and spreads well over the head hair.
  4: The solution for application is easy to scoop with a brush, and spreads well over the head hair.
  3: The solution for application can be scooped with a brush, and spreads well over the head hair.
  2: The solution for application is hard to scoop with a brush.
  1: The solution for application is hard to scoop with a brush, and does not sufficiently spread over the head hair.

For each test, ten panelists performed the evaluation, and the average was rounded to the nearest whole number and shown in the table as a whole number.

[Hair-Dyeing Evaluation]

The proper amount of hair dye solution for application applied to the head hair in the above operability test was left on at 30° C. for 30 minutes. Subsequently, the hair dye application liquid was rinsed off, and the hair was washed once with a shampoo and treated once with a conditioner. The head hair was then dried with a drier, followed by visual observation to evaluate the hair-dyeing power.

As a result, the head hairs dyed using the oxidation hair dyes of Examples 1 to 12 each had a deep hue.

[Temporal Stability Test]

To 3 g of the powder hair dye composition of each of Examples 1 to 13 and Comparative Examples 1 to 3 immediately after preparation (product at the time of preparation), 30 ml of water was added and mixed to give a hair dye solution for application. In addition, to 3 g of the powder hair dye composition of each of Examples 1 to 13 and Comparative Examples 1 to 3 after being stored at 50° C. for one month (product stored at 50° C.), 30 ml of water was added and mixed to give a hair dye solution for application. In the operation of applying each hair dye solution for application to the head hair using a brush, operability and viscosity were compared between the product at the time of preparation and the product stored at 50° C., and the temporal stability was evaluated based on the following criteria.

5: Viscosity and operability are equal between the product at the time of preparation and the product stored at 50° C.
  4: Viscosity of the product stored at 50° C. is slightly lower than that of the product at the time of preparation, but its operability is equal.
  3: Viscosity of the product stored at 50° C. is lower than that of the product at the time of preparation, but its operability is not problematic.
  2: Viscosity of the product stored at 50° C. is lower than that of the product at the time of preparation, and its operability is slightly inferior.
  1: The product stored at 50° C. has lower viscosity than the product at the time of preparation and falls down from applied hair.

For each test, ten panelists performed the evaluation, and the average was rounded to the nearest whole number and shown in the table as a whole number.

TABLE 1

|   |   | Examples |   |   |   |   |   |
|---|---|---|---|---|---|---|---|
|   |   | 1 | 2 | 3 | 4 | 5 | 6 |
| A | Sodium percarbonate | 25 | 25 | 25 | 25 | 11 | 55 |
| B | Sodium carboxymethyl cellulose | 10 | 10 | 20 | 25 | 10 | 10 |
| C | Xanthan gum | 5 | 10 | 10 | 5 | 10 | 10 |
|   | Hydroxyethyl cellulose | — | — | — | — | — | — |
|   | Polyquaternium-10 | — | — | — | — | — | — |
|   | Guar hydroxypropyltrimonium chloride | — | — | — | — | — | — |
|   | Highly polymerized polyethylene glycol | — | — | — | — | — | — |
|   | Carboxyvinyl polymer | — | — | — | — | — | — |
|   | Acrylate-alkyl methacrylate copolymer | — | — | — | — | — | — |
|   | Magnesium stearate | 0.5 | 0.5 | 0.5 | 0.5 | 0.5 | 0.5 |
|   | Sodium sulfate | 46 | 41 | 31 | 31 | 55 | 11 |

TABLE 1-continued

|  | Examples | | | | | |
| --- | --- | --- | --- | --- | --- | --- |
|  | 1 | 2 | 3 | 4 | 5 | 6 |
| p-Phenylenediamine sulfate | 11.5 | 11.5 | 11.5 | 11.5 | 11.5 | 11.5 |
| m-Aminophenol sulfate | 2 | 2 | 2 | 2 | 2 | 2 |
| Total | 100 | 100 | 100 | 100 | 100 | 100 |
| Content of component A at the time of use | 2.27 | 2.27 | 2.27 | 2.27 | 1.00 | 5.00 |
| Total content of component B and component C at the time of use | 1.36 | 1.82 | 2.73 | 2.73 | 1.82 | 1.82 |
| B/C | 2 | 1 | 2 | 5 | 1 | 1 |
| Viscosity | 4840 | 10080 | 17360 | 15890 | 9580 | 10960 |
| Miscibility | 5 | 4 | 4 | 5 | 4 | 4 |
| Operability | 4 | 5 | 5 | 5 | 5 | 5 |
| Temporal stability | 4 | 5 | 5 | 4 | 5 | 3 |

TABLE 2

|  |  | Examples | | | | | | |
| --- | --- | --- | --- | --- | --- | --- | --- | --- |
|  |  | 7 | 8 | 9 | 10 | 11 | 12 | 13 |
| A | Sodium percarbonate | 25 | 25 | 25 | 25 | 25 | 25 | 25 |
| B | Sodium carboxymethyl cellulose | 10 | 10 | 10 | 10 | 10 | 10 | 10 |
| C | Xanthan gum | — | — | — | — | — | — | 10 |
|  | Hydroxyethyl cellulose | 10 | — | — | — | — | — | — |
|  | Polyquaternium-10 | — | 10 | — | — | — | — | — |
|  | Guar hydroxypropyltrimonium chloride | — | — | 10 | — | — | — | — |
|  | Highly polymerized polyethylene glycol | — | — | — | 10 | — | — | — |
|  | Carboxyvinyl polymer | — | — | — | — | 10 | — | — |
|  | Acrylate-alkyl methacrylate copolymer | — | — | — | — | — | 10 | — |
|  | Magnesium stearate | 0.5 | 0.5 | 0.5 | 0.5 | 0.5 | 0.5 | 0.5 |
|  | Sodium sulfate | 41 | 41 | 41 | 41 | 41 | 41 | 54.5 |
|  | p-Phenylenediamine sulfate | 11.5 | 11.5 | 11.5 | 11.5 | 11.5 | 11.5 | — |
|  | m-Aminophenol sulfate | 2 | 2 | 2 | 2 | 2 | 2 | — |
|  | Total | 100 | 100 | 100 | 100 | 100 | 100 | 100 |
|  | Content of component A at the time of use | 2.27 | 2.27 | 2.27 | 2.27 | 2.27 | 2.27 | 2.27 |
|  | Total content of component B and component C at the time of use | 1.82 | 1.82 | 1.82 | 1.82 | 1.82 | 1.82 | 1.82 |
|  | B/C | 1 | 1 | 1 | 1 | 1 | 1 | 1 |
|  | Viscosity | 11260 | 6280 | 6080 | 3980 | 4120 | 4020 | 9070 |
|  | Miscibility | 4 | 4 | 4 | 3 | 3 | 3 | 4 |
|  | Operability | 5 | 5 | 5 | 4 | 4 | 4 | 5 |
|  | Temporal stability | 3 | 3 | 3 | 3 | 3 | 3 | 5 |

TABLE 3

|  |  | Comparative Examples | | |
| --- | --- | --- | --- | --- |
|  |  | 1 | 2 | 3 |
| A | Sodium percarbonate | 25 | 25 | 66 |
| B | Sodium carboxymethyl cellulose | 30 | 0 | 10 |
| C | Xanthan gum | 0 | 30 | 10 |
|  | Magnesium stearate | 0.5 | 0.5 | 0.5 |
|  | Sodium sulfate | 31 | 31 | 0 |
|  | p-Phenylenediamine sulfate | 11.5 | 11.5 | 11.5 |
|  | m-Aminophenol sulfate | 2 | 2 | 2 |
|  | Total | 100 | 100 | 100 |
|  | Content of component A at the time of use | 2.27 | 2.27 | 6.00 |
|  | Total content of component B and component C at the time of use | 2.73 | 2.73 | 1.82 |
|  | B/C | — | — | 1 |
|  | Viscosity | 16160 | 25780 | 9400 |
|  | Miscibility | 5 | 1 | 4 |
|  | Operability | 5 | 1 | 5 |
|  | Temporal stability | 1 | 5 | 2 |

The above results led to the following consideration. It was considered that in the examples of this application, because the component (A) to component (C) were contained, and also the content of the component (A) at the time of use was within the certain range, the miscibility, operability, and temporal stability were improved in a well-balanced manner.

In terms of making the amount of component (A) at the time of storage within the suitable range and improving the temporal stability, it was considered preferable that the upper limit of the content of the component (A) at the time of use should be about 3 to 4 mass % (Comparative Example 3, Example 6).

In terms of improving the miscibility, operability, and temporal stability in a well-balanced manner, it was considered preferable that the total content of the component (B) and the component (C) at the time of use should be 1.5 to 3 mass % (Examples 1 to 4).

In terms of improving the miscibility, operability, and temporal stability in a well-balanced manner, it was considered preferable that the component (C) should be xanthan gum, hydroxyethyl cellulose, or a cationized polymer, still more preferably xanthan gum. Xanthan gum significantly suppressed the deterioration of operability during long-term storage (Example 2, Examples 7 to 12).

Meanwhile, in Comparative Example 1 containing no component (C), the product stored at 50° C. fell down from applied hair, and the well-balanced effect as in the examples was not achieved. In Comparative Example 2 containing no component (B), although the temporal stability was excellent, the miscibility and operability had low ratings in the first place. Thus, similarly to Comparative Example 1, the well-balanced effect was not achieved. In Comparative Example 3 where the content of the component (A) at the time of use was more than 5 mass %, although the product stored at 50° C. did not fall down from applied hair, the temporal stability had a low rating, and the well-balanced effect as in the examples was not achieved. Accordingly, in the case where sodium percarbonate, sodium carboxymethyl cellulose, and a thickener other than sodium carboxymethyl cellulose are merely used together, viscosity and operability may decrease during long-term storage.

INDUSTRIAL APPLICABILITY

This application provides a powder hair dye composition having excellent miscibility with a liquid medium such as water, excellent operability at the time of application to hair, and excellent temporal stability during long-term storage.

This application provides a method for dyeing hair, which offers excellent operability at the time of application to hair. According to the method for dyeing hair, as long as certain conditions, such as to use the powder hair dye composition disclosed in this application, are satisfied, the operability is excellent even when the powder hair dye composition is used after long-term storage.

What is claimed is:

1. A powder hair dye composition comprising the following component (A) to component (C), the content of the component (A) at the time of use being 1 to 5 mass %:
   (A) sodium percarbonate;
   (B) sodium carboxymethyl cellulose; and
   (C) a thickener other than the component (B),
   wherein a mixing ratio on mass basis between the powder hair dye composition and a liquid medium at the time of use is represented by powder hair dye composition: liquid medium=1:7 to 1:15, and
   wherein a viscosity at the time of use is 1,000 to 30,000 mPa·s.

2. The powder hair dye composition according to claim 1, wherein the powder hair dye composition satisfies the following conditions (1) and/or (2):
   (1) the content of the component (B) at the time of use is 0.8 to 3 mass %;
   (2) the content of the component (C) at the time of use is 0.4 to 1.5 mass %.

3. The powder hair dye composition according to claim 1, wherein the total content of the component (B) and the component (C) is 1.5 to 3 mass % at the time of use.

* * * * *